US010058547B2

(12) United States Patent
Rey et al.

(10) Patent No.: US 10,058,547 B2
(45) Date of Patent: *Aug. 28, 2018

(54) NALOXONE SINGLE AGENT AND MULTILAYER TABLETS

(71) Applicant: Develco Pharma Schweiz AG, Prattein (CH)

(72) Inventors: Hélène Rey, Kembs (FR); Olaf Mundszinger, Efringen-Kirchen (DE); Isabelle Golfier, Bantzenheim (FR); Silvia Jakob, Bernau (DE); Oliver Rusch, Basel (CH)

(73) Assignee: Develco Pharma Schweiz AG, Pratteln (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,856

(22) Filed: Sep. 2, 2016

(65) Prior Publication Data

US 2016/0367550 A1 Dec. 22, 2016

Related U.S. Application Data

(63) Continuation of application No. 14/563,555, filed on Dec. 8, 2014, now Pat. No. 9,456,986.

(30) Foreign Application Priority Data

| Dec. 11, 2013 | (EP) | 13005759 |
| Dec. 11, 2013 | (EP) | 13005760 |
| Dec. 11, 2013 | (EP) | 13005761 |

(51) Int. Cl.
| *A61K 9/20* | (2006.01) |
| *A61K 31/485* | (2006.01) |
| *A61K 9/00* | (2006.01) |
| *A61K 9/50* | (2006.01) |
| *A61K 9/24* | (2006.01) |
| *A61K 9/28* | (2006.01) |

(52) U.S. Cl.
CPC .......... *A61K 31/485* (2013.01); *A61K 9/0004* (2013.01); *A61K 9/0053* (2013.01); *A61K 9/0056* (2013.01); *A61K 9/2009* (2013.01); *A61K 9/209* (2013.01); *A61K 9/2013* (2013.01); *A61K 9/2027* (2013.01); *A61K 9/2054* (2013.01); *A61K 9/2077* (2013.01); *A61K 9/2095* (2013.01); *A61K 9/28* (2013.01); *A61K 9/5084* (2013.01)

(58) Field of Classification Search
None
See application file for complete search history.

(56) References Cited

U.S. PATENT DOCUMENTS

| 8,846,090 B2 * | 9/2014 | Brogmann | A61K 9/1617 424/464 |
| 9,456,986 B2 | 10/2016 | Rey et al. | |

| 2013/0090349 A1 | 4/2013 | Geissler et al. | |
| 2015/0108033 A1* | 4/2015 | Vamvakas | A61K 9/4866 206/531 |
| 2015/0216806 A1 | 8/2015 | Borody | |
| 2015/0238420 A1 | 8/2015 | Rey et al. | |

FOREIGN PATENT DOCUMENTS

| DE | 4325465 A1 | 2/1995 |
| EP | 2425825 A1 | 3/2012 |
| WO | WO-95/20947 A1 | 8/1995 |
| WO | WO-98/25613 A2 | 6/1998 |
| WO | WO-03/007802 A2 | 1/2003 |
| WO | WO-2009/085778 A1 | 7/2009 |
| WO | WO-2011/117306 A1 | 9/2011 |
| WO | WO-2012/052169 A2 | 4/2012 |

OTHER PUBLICATIONS

European Pharmacopoeia 7.3, 2.9.3 "Dissolution Test for Solid Dosage Forms" (2012) (7 pages).
European Pharmacopoeia 7.7, 4.1.3 "Buffer Solutions" (2013) (6 pages).
Shah V. et al "In Vitro Dissolution Profile Comparison—Statistics and Analysis of the Similarity Factor f2", Pharm Res. (1998) 15(6):889-96.
Preliminary Amendment dated Mar. 23, 2015 to the U.S. Patent and Trademark Office for U.S. Appl. No. 14/563,555, filed Dec. 8, 2014 and granted as U.S. Pat. No. 9,456,986 on Oct. 4, 2016 (Applicant—Develco Pharma Schweiz AG; Inventor—Helene Rey et al) (7 pages).
Non Final Rejection dated Nov. 19, 2015 by the U.S. Patent and Trademark Office for U.S. Appl. No. 14/563,555, filed Dec. 8, 2014 and granted as U.S. Pat. No. 9,456,986 on Oct. 4, 2016 (Applicant—Develco Pharma Schweiz AG; Inventor—Helene Rey et al) (4 pages).
Response to Non Final Rejection dated Feb. 16, 2016 to the U.S. Patent and Trademark Office for U.S. Appl. No. 14/563,555, filed Dec. 8, 2014 and granted as U.S. Pat. No. 9,456,986 on Oct. 4, 2016 (Applicant—Develco Pharma Schweiz AG; Inventor—Helene Rey et al) (8 pages).
Notice of Allowance dated Jun. 2, 2016 by the U.S. Patent and Trademark Office for U.S. Appl. No. 14/563,555, filed Dec. 8, 2014 and granted as U.S. Pat. No. 9,456,986 on Oct. 4, 2016 (Applicant—Develco Pharma Schweiz AG; Inventor—Helene Rey et al) (9 pages).

(Continued)

Primary Examiner — Susan T Tran
(74) Attorney, Agent, or Firm — Ballard Spahr LLP

(57) ABSTRACT

The present invention relates to a solid oral pharmaceutical composition comprising naloxone, or a pharmaceutical acceptable salt thereof, as an active substance, wherein the composition releases the active substance in a prolonged manner. In order to provide a composition that is suitable for an administration period of at least twelve-hours for the treatment of opioid-induced constipation, it is proposed that the composition should have an in vitro release rate of the active substance measured using the paddle stirrer method according to Ph. Eur. at 75 rpm in 500 ml 0.1 N hydrochloric acid at 37° C., of 0% to 75% in 2 h, of 3% to 95 % in 4 h, of 20% to 100% in 10 h, of 30% to 100% in 16 h, of 50% to 100% in 24 h, and of more than 80% in 36 h, wherein the composition has a $IC_{50}/C_{max}$ value of at least 40. In an alternative embodiment, the composition can be a multilayer tablet.

20 Claims, 1 Drawing Sheet

(56) References Cited

OTHER PUBLICATIONS

Issue Notification dated Sep. 14, 2016 by the U.S. Patent and Trademark Office for U.S. Appl. No. 14/563,555, filed Dec. 8, 2014 and granted as U.S. Pat. No. 9,456,986 on Oct. 4, 2016 (Applicant—Develco Pharma Schweiz AG; Inventor—Helene Rey et al) (1 page).
Hermanns K. et al.: "Prolonged-release oxycodone/naloxone in the treatment of neuropathic pain: results from a large observational study" Expert Opinion on Pharmacotherapy, vol. 13, No. 3,(2012), pp. 299-311.
Meissner W. et al.: "A randomised controlled trial with prolonged-release oral oxycodone and naloxone to prevent and reverse opioid-induced constipation", European Journal of Pain, vol. 13, No. 1, (2009), pp. 56-64.
European Search Report dated Oct. 26, 2016 by the European Patent Office for EP Application No. 16186993.8 (Applicant—Develco Pharma Schweiz) (9 pages).
Non-Final Office Action dated Oct. 5, 2017 by the U.S. Patent and Trademark Office for U.S. Appl. No. 15/255,868, filed Sep. 2, 2016 and published as US 2017/0087150 on Mar. 30, 2017 (Inventor—Rey et al.; Applicant—Develco Pharma Schweiz AG; (9 pages).
U.S. Appl. No. 14/563,555, filed Dec. 8, 2014, Rey et al.
U.S. Appl. No. 15/255,868, filed Sep. 2, 2016, Rey et al.

\* cited by examiner

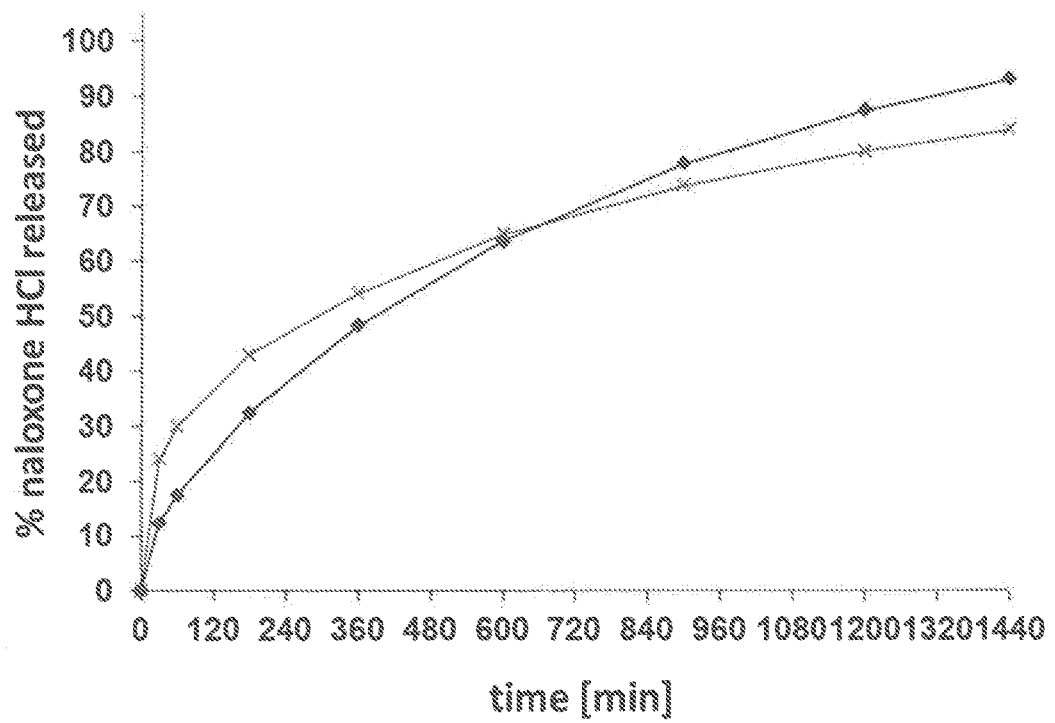

NALOXONE SINGLE AGENT AND MULTILAYER TABLETS

BACKGROUND

The present invention relates to a solid oral pharmaceutical composition comprising naloxone, or a pharmaceutical acceptable salt thereof, wherein the composition releases the active substance in a prolonged manner.

The present invention also relates to a solid oral pharmaceutical composition comprising naloxone, or a pharmaceutical acceptable salt thereof, for the treatment of opioid-induced constipation.

The present invention relates to a tablet comprising an opioid agonist, or a pharmaceutical acceptable salt thereof, as well as an opioid antagonist, or a pharmaceutically acceptable salt thereof, as active substances, wherein the tablet releases the active substances in a prolonged manner.

The present invention also relates to a solid oral pharmaceutical composition comprising naloxone, or a pharmaceutical acceptable salt thereof, for use in for the treatment of opioid-induced constipation.

Constipation is a major side effect of opioid analgesics administration. It is one of the most common side effects and is particularly predominant in long-term opioid administration therapies, occurring in approximately 85% of patients, in contrast to other opioid-induced side effects, opioid-induced constipation is a chronic phenomenon, the intensity of which does not decrease over the course of the treatment. The effect of the opioids on the gut mobility is probably due to binding of the opioids to the opioid receptors of the gastrointestinal tract, which are present there at a relatively high density.

The aim of the a therapy proposed here is to neutralize this peripheral side effect of opioids because opioid-induced constipation can be uncomfortable and very painful, and often leads to the discontinuation of the opioid-based therapy, and thus endangers the success of the treatment with the opioids. Since it can be assumed that the opioid-induced constipation is caused directly and locally over the entire intestine through binding to the opioid receptors, this side effect should be eliminated through the use of opioid antagonists. However, the use of opioid antagonists only makes sense if the antagonistic effect is limited to the intestine and does not cancel the main analgesic effect.

Naloxone is a suitable opioid antagonist for the treatment of opioid-induced constipation. Naloxone is rapidly and completely absorbed after oral administration and because the substance is subject to extensive first-pass metabolism, only small amounts of unmetabolised naloxone are available to the system. The vast majority of the applied substance is found in blood in the form of inactive or only mildly active metabolites such as naloxone-3-glucuronide or beta-6-naloxol. In suitable doses, naloxone is an ideal candidate for remedying opioid-induced constipation, in the intestine it is present as an active substance and can thus counter the paralysing effect of the opioid on the gastrointestinal tract, while after absorption it is largely metabolised during the first passage in the liver, and thereby becomes inactive. The analgesic effect of the opioids is thus not affected.

Since the paralysis does not only affect the duodenum and the upper part of the small intestine, but the entire gastrointestinal tract, the opioid-induced constipation cannot be treated successfully with a composition that releases the naloxone rapidly. WO 2011/117306 discloses a two-layer tablet, which in one layer contains an opioid agonist, and in another layer an opioid antagonist, wherein the tablet quickly releases both active substances. The advantage of this double-layer is to suppress the side effects of the opioid agonist, but it does not focus on suppression of the opioid-induced constipation.

The combined preparation Targin® is available on the market and comprises a mixture of the opioid agonist oxycodone in the form of a hydrochloric salt, and the opioid antagonist naloxone also in the form of a hydrochloric salt. In this preparation, the active substances are released in a prolonged manner. It is therefore suitable for the parallel treatment of pain and opioid-induced constipation. However, this monolithic formulation has the disadvantage that the release rates of the two active substances are fixed, individualised treatments are therefore difficult to optimise.

In addition, infusion solutions available on the market for the treatment of opioid poisoning are only naloxone combined preparations, in which naloxone and the opiate are present in a fixed proportion to each other. However, for the treatment of opioid-induced constipation, it would be desirable to have single agent naloxone preparations, since this would allow administering naloxone both independently of the nature of the opiate and in variable doses. The desired quantity of naloxone could therefore be applied, which would lead to an optimal treatment. Naloxone single agent preparations are described in the patent literature, such as in WO 98/25613 A2. However, the release of naloxone from these compositions is dependent on the ambient pH in the gastrointestinal tract. A uniform application of naloxone to the entire gastrointestinal tract, and therefore an optimal treatment are thus not possible with such products.

DESCRIPTION OF THE INVENTION

The objective of the present invention is to provide a solid oral pharmaceutical composition comprising naloxone, or a pharmaceutical acceptable salt thereof, as an active substance, wherein the composition releases the active substance naloxone in a prolonged manner, and is suitable for an administration period of at least twelve-hours, for the treatment of opioid-induced constipation.

This objective is achieved by a solid oral pharmaceutical composition comprising naloxone, or a pharmaceutical acceptable salt thereof, as an active substance, wherein the composition releases the active substance in a prolonged manner, and the in vitro release rate of the active substance naloxone, measured using the paddle stirrer method according to Ph. Eur. at 75 rpm in 500 ml 0.1 N hydrochloric acid at 37° C., is of 0% to 75% in 2 h, of 3% to 95% in 4 h, of 20% to 100% in 10 h, of 30% to 100% in 16 h, of 50% to 100% in 24 h, and of more than 80% in 36 h.

It was observed that the composition according to the invention, with its release profile, was suitable for an administration period of at least twelve-hours for the treatment of opioid-induced constipation. Accordingly it possesses a relatively high level of patient compliance.

The in vitro release rate is determined using the paddle stirrer apparatus (apparatus 2) with the paddle stirrer method according to Ph. Eur. (Europäisches Arsneibuch, 7th edition, 3rd supplement, 2.9.3 "Wirkstofffreisetzung aus festen Arzneiformen", pages 5519-5526) at 75 rpm in 500 ml 0.1 N hydrochloric acid at 37° C. The amount of released active substance is preferably determined by UV-detection at 220 nm.

The opioid-induced constipation which can be treated by the composition according to the invention can be caused by any opioid analgesic or opioid analgesic analogue, or by any of their salts or mixtures. Examples of such analgesics are the following: alfentanil, allylprodine, alphaprodine, anileridine, benzylmorphine, bezitramide, buprenorphine, butorphanol, clonitazene, codeine, besomorphine, dextromoramide, dezocine, diampromide, diamorphone, dihydrocodeine, dihydromorphine, dimenoxadol, Dimepheptanol, dimethylthiambutene, dioxapbetyl butyrate, dipipanone, eptazocine, ethoheptazine, ethylmethylthiambutene, ethylmorphine, etonitazene, fentanyl heroin, hydrocodone, hydromorphone, hydroxypethidine, isomethadone, ketobemidone, levorphanol, levophenacylmorphane, lofentanil, meperidine, meptazinol, metazocine, methadone, metopone, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphane, phenazocine, phenoperidine, piminodine, piritramide, propheptazine, promedol, properidine, propoxyphene, sufentanil, tilidine, and tramadol, wherein hydrocodone, morphine, hydromorphone, oxycodone, buprenorphine, codeine, fentanyl, levorphanol, meperidine, methadone, levomethadone, and dextromethadone are particularly preferred according to the invention.

In a preferred embodiment of the invention, the composition has an in vitro release rate of the active substance of 0% to 50% in 2 h, of 5% to 95% in 4 h, of 20% to 90% in 10 h, of more than 70% in 18 h, and of more than 80% in 24 h.

In a more preferred embodiment of the invention, the composition has an in vitro release rate of the active substance of 0% to 38% in 2 h, of 5% to 55% in 4 h, and of 20% to 75% in 10 h.

According to another preferred embodiment of the invention, the composition has an in vitro release rate of the active substance of 0% to 50% in 1 h, of 10% to 95% in 4 h, of 35% to 100% in 8 h, of 55% to 100% in 12 h, of 70% to 100% in 16 h, and of more than 90% in 24 h.

According to another preferred embodiment of the invention, the composition has an in vitro release rate of the active substance of 0% to 30% in 1 h, of 0% to 40% in 2 h, of 3% to 55% in 4 h, of 10% to 65% in 8 h, of 20% to 75% in 12 h, of 30% to 88% in 16 h, of 50% to 100% in 24 h, and of more than 80% in 36 h.

In a further preferred embodiment of the invention, the composition has an in vitro release rate of the active substance of 10% to 30% in 1 h, of 17% to 37% in 2 h, of 27% to 47% in 4 h, of 40% to 60% In 8 h, of 50% to 70% in 12 h, of 60% to 80% in 16 h, of 80% to 100% in 24 h.

In a particularly preferred embodiment of the invention, the composition releases the active substance naloxone independently of the ambient pH of the gastrointestinal tract. This ensures that the entire gastrointestinal tract can be evenly and continuously supplied with naloxone, or an acceptable salt thereof. A further optimisation of the treatment is thereby achieved. The pH-independent release of the active substance from the composition of the invention can be achieved through the choice of suitable pharmaceutical excipients that will be known to the person skilled in the art. Local pH values in the gastrointestinal tract are from about 1.2 (in the stomach), to shout 6.8 in the colon.

The release of the active substance from the composition of the invention that is independent from the pH of the gastrointestinal is preferably understood to mean that the similarity factor f2 between a first in vitro release at s pH of 1.2 to 6.8 and a second in vitro release at any other pH of 1.2 to 6.8 is larger or equal to 50.

The similarity factor f2 is determined according to SHAH V. P., TSONG Y., SATHE P., & LIU J. P. (1998), "In vitro dissolution profile comparison-statistics and analysis of the similarity factor, f2", Pharmaceutical Research, 15, 889-896. Specifically, the similarity factor f2 is calculated by the following formula:

$$f_2 = 50 * \log_{10}\left(\left[1 + \frac{1}{n}\sum_{t=1}^{n}(R_t - T_t)^2\right]^{0.5} * 100\right)$$

In this equation, Rt and Tt represent the released quantities of active substance at time point t at the first and second pH, n is the number of time points. The f2 factor is determined under the following conditions: a) the minimal number of time points for one release is 3 (time point 0 is excluded); b) the time points for the first and the second pH should be equal; c) for each time point, and for each pH, the released quantity is indicated as the mean value of 12 measurements; d) no more than one mean value measured above a release of 85% can be taken into account for the calculation; e) the relative standard deviation or coefficient of variation of the release at a given pH should be smaller than 20% for the first time point and smaller than 10% for the second, and every subsequent time point.

The in vitro release profiles used for the calculation of the f2 factor are determined using the paddle stirrer apparatus (apparatus 2) with the paddle stirrer method according to Ph, Eur. (Europäisches Arzneibuch, 7th edition, 3rd supplement, 2.9.3 "Wirkstofffreisetzung aus festen Arzneiformen", pages 5519-5526) at 75 rpm in 500 ml buffer (according to the Europaisches Arzneibuch, 7th edition, 7th supplement, 4.13 "Pufferlösungen", pages 7671-7679) at 37° C. The amount of released active substance is determined by UV-detection at 220 nm.

In a further preferred embodiment of the invention, the composition comprises a matrix, which releases the active ingredient in a prolonged manner. The active substance can be released in a prolonged manner inexpensively, particularly when it is contained in a matrix that prolongs its release.

The composition according to the invention may comprise a matrix, which releases naloxone, or a pharmaceutically acceptable salt thereof, in a prolonged manner. The matrix according to the invention is preferably a so-called scaffold matrix, which can be swelling or non-swelling, or can be a so-called eroding matrix. The matrix can also have properties of both scaffold and eroding matrixes.

In the case of a scaffold matrix, the active substance is incorporated into the matrix structure. The active substance is gradually dissolved by the digestive juices from the loaded scaffold matrix during the transport through the gastrointestinal tract. At the end of the process, the matrix scaffold is excreted in more or less unchanged form, or in a swollen form, in contrast, with an eroding matrix, the matrix is degraded, or eroded, which leads to active substance particles being exposed at the surface, and dissolved. The release rate therefore depends on the matrix degradation or erosion rate.

For the purpose of forming a largely stable scaffold matrix with an appropriate active substance release rate, a further preferred embodiment of the invention is a composition with a matrix that comprises one or several water-soluble matrix-forming agents.

According to a further preferred embodiment of the invention, the matrix of the composition is water-insoluble.

In another preferred embodiment of the invention, the matrix of the composition comprises one or several matrix-forming agents selected from the group consisting of cellulose esters, polyethylene oxide, polyvinylpyrrolidone/polyvinyl acetate mixtures, methacrylate-acrylate copolymers, waxes, fats such as glycerol esters, and fatty alcohols. The substance classes mentioned here are particularly suitable as matrix-forming agents for the composition of the invention. However, particularly preferred is the use of a mixture of polyvinyl acetate and polyvinylpyrrolidone, and/or a glycerol dibehenic acid ester as matrix-forming agent.

In a further preferred embodiment of the invention, the composition is free of film-coated, naloxone-containing particles, wherein the coating causes the prolonged release of the naloxone.

According to a further preferred embodiment of the invention, the composition can be formed by direct compression, since this is particularly inexpensive.

According to another preferred embodiment of the invention, the composition is in the form of a tablet, capsule, granule, a micro tablet, extruded particles or granules compressed into a tablet.

In a further preferred embodiment of the invention, the composition is designed as a once-a-day formulation, or a twice-a-day formulation.

Naloxone, or a pharmaceutically acceptable salt thereof, is the active substance of the composition according to the invention, wherein naloxone hydrochloride is particularly preferred due to its solubility and stability. One or several additional active substances can be present in the composition.

Naloxone, or a pharmaceutically acceptable salt thereof, in the composition according to the invention is preferably present in an amount from 0.1 to 500 mg, more preferably from 1 mg to 50 mg and even more preferably in an amount from 3 mg, 8 mg, 12 mg, 24 mg or 48 mg.

The present invention further relates to the use of the composition according to the invention for the treatment of opioid-induced constipation.

Regarding the composition which is particularly suited for a twice-a-day administration, the present invention further relates to a solid oral pharmaceutical composition comprising naloxone, or a pharmaceutically acceptable salt thereof, as an active substance, wherein the composition releases the active substance in a prolonged manner, and the in vitro release rate of the active substance, measured using the paddle stirrer method according to Ph. Eur. at 75 rpm in 500 ml 0.1 N hydrochloric acid at 37° C., is of 5% to 50% in 1 h, of 10% to 75% in 2 h, of 20% to 95% in 4 h of 40% to 100% in 8 h, of more than 50% in 12 h, of more than 70% in 18 h, and of more than 80% in 24 h.

Regarding the composition which is particularly suited for a twice-a-day administration, the present invention further relates to a solid oral pharmaceutical composition comprising naloxone, or a pharmaceutically acceptable salt thereof, as an active substance, wherein the composition releases the active substance in a prolonged manner, and the in vitro release rate of the active substance, measured using the paddle stirrer method according to Ph. Eur. at 75 rpm in 500 ml 0.1 N hydrochloric acid at 37° C., is of 20% to 50% in 1 h, of 40% to 75% in 2 h, of 60% to 95% in 4 h, of 80% to 100% in 8 h, and of 90% to 100% in 12 h.

Regarding the composition which is particularly suited for a once-a-day administration; the present invention further relates to a solid oral pharmaceutical composition comprising naloxone, or a pharmaceutically acceptable salt thereof, as an active substance, wherein the composition releases the active substance in a prolonged manner, and the in vitro release rate of the active substance, measured using the paddle stirrer method according to Ph. Eur, at 75 rpm in 500 ml 0.1 N hydrochloric acid at 37° C., is of 0% to 50% in 1 h, of 0% to 75% in 2 h, of 10% to 95% in 4 h, of 35% to 100% in 8 h, of 55% to 100% in 12 h, of 70% to 100% in 16 h and of more than 90% in 24 h.

Regarding the composition which is particularly suited for a once-a-day administration, the present invention further relates to a solid oral pharmaceutical composition comprising naloxone, or a pharmaceutically acceptable salt thereof, as an active substance, wherein the composition releases the active substance in a prolonged manner, and the in vitro release rate of the active substance, measured using the paddle stirrer method according to Ph. Eur. at 75 rpm in 500 ml 0.1 N hydrochloric acid at 3% is of 0% to 30% in 1 h, of 0% to 40% in 2 h, of 3% to 55% in 4 h, of 10% to 60% in 8 h, of 20% to 75% in 12 h, of 30% to 88% in 16 h, of 50% to 100% in 24 h, and of more than 80% in 36 h.

Regarding the composition which is particularly suited for a once-a-day administration, the present invention further relates to a solid oral pharmaceutical composition comprising naloxone, or a pharmaceutically acceptable salt thereof, as an active substance, wherein the composition releases the active substance in a prolonged manner, and the in vitro release rate of the active substance, measured using the paddle stirrer method according to Ph. Eur. at 75 rpm in 500 ml 0.1 N hydrochloric acid at 37° C., is of 10% to 30% in 1 h, of 17% to 37% in 2 h, of 27% to 47% in 4 h, of 40% to 60% in 8 h, of 50% to 70% in 12 h, of 60% to 80% in 16 h, and of 80% to 100% in 24 h.

In accordance with good patient compliance, a further preferred embodiment of the invention is a composition, wherein the composition is preferably a tablet or a capsule, which has an in vitro release rate of the active substance, measured using the paddle stirrer method according to Ph. Eur. at 75 rpm in 500 ml 0.1 N hydrochloric acid at 37° C., of 0% to 75% in 2 h, of 3% to 95% in 4 h, of 20% to 100% in 10 h, of 30% to 100% in 16 h, of 50% to 100% in 24 h, and of more than 80% in 36 h.

A further preferred embodiment of the invention is providing a composition that is suitable for the treatment of opioid-induced constipation for at least 12 h, provided that the composition has an in vitro release rate of the active substance of 0% to 50% in 2 h, of 5% to 95% in 4 h, of 20% to 90% in 10 h, of more than 70% in 18 h, and of more than 80% in 24 h.

The release rate is, in accordance with the invention, controlled by adjusting the mass ration of naloxone to matrix-forming agent. In a preferred embodiment, the mass ratio of naloxone to matrix-forming agent is 1:1, more preferably 1:2, more preferably 1:5, more preferably 1:6, more preferably 1:7; even more preferably 1:8, yet more preferably 1:9 and most preferably 1:10.

The composition of the invention is characterised in that through the prolonged release the concentration of naloxone in the plasma is low. Its maximum plasma concentration ($C_{max}$) is about 20× lower during the active course compared to a composition without prolonged release, and about 100× lower compared with an intravenously administered composition.

However, the inhibition of the receptors over the active course is better, in addition to providing the constipation prevention effect of naloxone, the low bioavailability in the system also ensures a reduced likelihood and/or severity of the side effects.

Since the naloxone inhibitory concentrations ($IC_{50}$) for opioid receptors ($\mu$, $\delta$ and $\kappa$) are known, the assessment of the risk factor of a tablet can be calculated with the ratio $IC_{50}/C_{max}$. With the $IC_{50}$ of $\mu$ receptor, the value of $IC_{50}/C_{max}$ for a tablet according to the invention with 48 mg of naloxone is 54. In general, the higher the value of $IC_{50}/C_{max}$, the lower the risk factor of the tablet according to the invention. Hereafter all values relating to the $IC_{50}$ are for the $\mu$ receptor.

In a preferred embodiment, the composition has an $IC_{50}/C_{max}$ value of at least 30. In a more preferred embodiment, the composition has an $IC_{50}/C_{max}$ value of at least 35. In an even more preferred embodiment, the composition has an $IC_{50}/C_{max}$ value of at least 40. In the most preferred embodiment, the composition has an $IC_{50}/C_{max}$ value of at least 50.

In a further embodiment, the composition additionally comprises at least one stabilizer, which protects the active substance. In a preferred embodiment, the at least one stabiliser is selected from the list comprising sulphur dioxide, sodium sulphite, sodium bisulphite, ascorbic acid and its derivatives and tocopherol, as well as its water- and fat-soluble derivatives, such as, for example, tocopherol acetate, sulphites, bisulphites and hydrogen sulphites of alkali, alkaline earth metals or other metals, paraben, BHA, BHT, gallates, as well as lower fatty acids, fruit acids, phosphoric acids, sorbic and benzoic acids as well as their salts, esters, derivatives and isomeric compounds, ascorbyl palmitate, lecithins, mono- and polyhydroxylated benzene derivatives, ethylenediaminetetraacetic acid and salts thereof, citraconic acid, cysteine, L-cysteine, conidendrin, diethyl carbonate, methylenedioxyphenols, cephalin, $\beta,\beta'$-dithiopropionic acid, biphenyl and other phenyl derivatives.

In a further embodiment, the composition additionally comprises at least one stabiliser, which protects the matrix. In a preferred embodiment, the at least one stabilizer is selected from the list comprising butylated hydroxytoluol, sulphur dioxide, sodium sulphite, sodium bisulphite, ascorbic acid and its derivatives and tocopherol, as well as its water- and fat-soluble derivatives, such as, for example, tocopherol acetate, sulphites, bisulphites and hydrogen sulphites of alkali, alkaline earth metals and other metals, paraben, BHA, BHT, gallates as well as lower fatty acids, fruit acids, phosphoric acids, sorbic and benzoic acids and their salts, esters, derivatives and isomeric compounds, ascorbyl palmitate, lecithins, mono- and polyhydroxylated benzene derivatives, ethylenediaminetetraacetic acid and their salts, citraconic acid, cysteine, L-cysteine, conidendrin, diethyl carbonate, methylenedioxyphenole, cephalin, $\beta,\beta'$-dithiopropionic acid, biphenyl and other phenyl derivatives.

In a further embodiment, the composition comprises at least one additive, wherein the additive is an emetic or a pungent agent drug, in a preferred embodiment, the composition comprises an additive, wherein this additive is a pungent agent, selected from the group comprising Allii sativi bulb, Asari rhizome cum herba, Calami rhizoma, capsici fructus (capsicum) capsici fructus acer (cayenne pepper), Rhizoma Curcumae Longae, Curcumae xanthorrhizae rhizoma, Galangae rhizoma, Semen Myristicae, Piperis nigri fructus (pepper), Sinapis albae (Erucae) Semen, Sinapis nigrae semen, Zedoariae rhizoma and Zingibers rhizome, preferably from the group consisting of capsici fructus (capsicum), capsici fructus acer (cayenne pepper) and Piperis nigri fructus (pepper).

In a preferred embodiment, the composition comprises at least one additive, wherein this additive is an emetic. In a preferred embodiment, the emetic is based on one or several substances from radix ipecacuanha (ipecac). In a preferred embodiment, the emetic is based on the substance emetine, in an alternative embodiment, the emetic is apomorphine.

In a further embodiment, the composition comprises a dye. In a preferred embodiment, the dye is selected from a group comprising red iron oxide, black iron oxide and indigo carmine.

In a further embodiment, the composition additionally comprises at least one non-steroid antirheumatic or an antihistamine.

In an alternative embodiment, the composition additionally comprises at least one water-soluble lubricant. In a preferred embodiment, the composition comprises at least one water-soluble lubricant selected from the group comprising adipic acid, fumaric acid, sodium benzoate and macrogol.

The aim of the present invention is also to provide a tablet, which comprises an opioid agonist, or a pharmaceutically acceptable salt thereof, and an opioid antagonist, or a pharmaceutically acceptable salt thereof, as active substances, and is suitable for the parallel treatment of pain and opioid-induced constipation, wherein the treatment can be easily optimised by means of the tablet.

The invention fulfils this aim through a multilayer tablet comprising at least
  a first active substance-containing layer, which contains as an active substance an opioid agonist, or a pharmaceutical acceptable salt thereof; and
  a second active substance-containing layer, which contains as an active substance an opioid antagonist, or a pharmaceutically acceptable salt thereof,
wherein at least the second active substance-containing layer releases the active substance in a prolonged manner. In a preferred embodiment, both the first and the second active substance-containing layers release the active substance in a prolonged manner. The multilayer tablet can also comprise additional active substances.

The multilayer tablet according to the invention is suitable for the parallel treatment of pain and opioid-induced constipation, wherein variable release kinetics for each active substance are easily achieved and individualised treatments can therefore easily be optimised.

The multilayer tablet of the invention has the further advantage that in each layer a different release retarding system can be used, such as sustained-release pellets coated with a release retardant, or a sustained-release matrix. This allows to easily and independently vary the release kinetics for each active substance and the proportion of the active substances, for tailoring the treatment to a patient.

The multilayer tablet of the invention also has the advantage that it enables a much more accurate dosage of the active substances. This is particularly important for small doses.

The tablet of the invention is also advantageous when the two active substances are not compatible with one another.

According to a particularly preferred embodiment of the invention, the multilayer tablet is a two-layer tablet. The multilayer tablet of the invention can be obtained as a two-layer tablet by a simple and therefore inexpensive process.

In a further preferred embodiment of the multilayer tablet according to the invention, the second active substance-containing layer comprises a matrix, which prolongs the release of the opioid antagonist, or a pharmaceutically acceptable salt thereof. A release-prolonging matrix can be obtained by a simple and therefore inexpensive process. The matrix can, according to the invention, preferably be a so-called scaffold matrix, which can be swelling or non-swelling, or a so-called eroding matrix. The matrix can also have properties of both scaffold and eroding matrixes.

In a scaffold matrix, the active substance is incorporated into the matrix structure. The active substance is gradually dissolved by the digestive juices from the loaded scaffold matrix during the transport through the gastrointestinal tract. When this is done, the matrix scaffold is excreted in more or less unchanged form, or in a swollen form. In contrast, with an eroding matrix, the matrix is degraded, or eroded, which leads to active substance particles being exposed at the surface, and dissolved. The release rate therefore depends on the matrix degradation or erosion rate.

According to a further preferred embodiment of the multilayer tablet of the invention, the matrix contains one or several water-insoluble matrix-forming agents. In an alternative embodiment, the matrix contains one or several water-soluble matrix-forming agents.

In another preferred embodiment of the multilayer table of the invention, the matrix of the composition comprises one or several matrix-forming agents selected from the group consisting of cellulose esters, polyethylene oxide, polyvinylpyrrolidone/polyvinyl acetate mixtures, methacrylate-acrylate copolymers, waxes, fats such as glycerol esters, and fatty alcohols. The substance classes mentioned here are particularly suitable as matrix-forming agents for the composition of the invention. However, particularly preferred is the use of a mixture of polyvinyl acetate and polyvinylpyrrolidone, and/or a glycerol dibehenic acid ester as matrix-forming agent.

The release rate is, in accordance with the invention, controlled by adjusting the mass ration of naloxone to matrix-forming agent. In a preferred embodiment, the mass ratio of naloxone to matrix-forming agent is 1:1, more preferably 1:2, more preferably 1:5, more preferably 1:6, more preferably 1:7, even more preferably 1:8, yet more preferably 1:9 and most preferably 1:10.

According to a further preferred embodiment of the multilayer tablet of the invention, the second active substance-containing layer releases the active substance, the opioid antagonist, or the pharmaceutically acceptable salt thereof, independently of the ambient pH of the gastrointestinal tract. This ensures that the entire gastrointestinal tract can be evenly and continuously supplied with naloxone, or an acceptable salt thereof. A further optimisation of the treatment is thereby achieved. The pH-independent release of the active substance from the multilayer tablet of the invention can be achieved through the choice of suitable pharmaceutical excipients that will be known to the person skilled in the art. Local pH values in the gastrointestinal tract are from about 1.2 (in the stomach), to about 7 in the colon.

In a further preferred embodiment of the multilayer tablet of the invention, the opioid antagonist is selected form a group consisting of naloxone, N-methylnalaxone and N-methylnaltrexone, as well as pharmaceutically acceptable salts thereof, wherein naloxone hydrochloride is particularly preferred.

In a further preferred embodiment of the multilayer tablet according to the invention, the opioid agonist, or the pharmaceutically acceptable salt thereof, of the first active substance-containing layer is present in the form of pellets which contain the opioid agonist and onto which a release retardant layer is applied.

In a preferred embodiment, the multilayer tablet of the invention has an $IC_{50}/C_{max}$ value for naloxone of at least 30. In a more preferred embodiment, the multilayer tablet has an $IC_{50}/C_{max}$ value of at least 35. In an even more preferred embodiment, the multilayer tablet has an $IC_{50}/C_{max}$ value of at least 40. In the most preferred embodiment, the multilayer tablet has an $IC_{50}/C_{max}$ value of at least 50.

In a further preferred embodiment of the multilayer tablet according to the invention the opioid agonist is selected from a group consisting of: alfentanil, allylprodine, alphaprodine, anileridine, benzylmorphine, bezitramide, buprenorphine, butorphanol, clonitazene, codeine, besomorphine, dextromoramide, dezocine, diampromide, diamorphone, dihydrocodeine, dihydromorphine, dimenoxadol, Dimepheptanol, dimethylthiambutene, dioxaphetyl butyrate, diplpanone, eptazocine, ethoheptazine, ethylmethylthlambutene, ethylmorphlne, etonitazene, fentanyl, heroin, hydrocodone, hydromorphone, hydroxypethidine, isomethadone, ketobemidone, levorphanol, levophenacylmorphane, lofentanil, meperidine, meptazinol, metazocine, methadone, metopone, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphane, phenazocine, phenoperidine, piminodine, piritramide, propheptazine, promedol, properidine, propoxyphene, sufentanil, tilidine, and tramadol, wherein hydrocodone, morphine, hydromorphone, oxycodone, buprenorphine, codeine, fentanyl, levorphanol, meperidine, methadone, levomethadone, and dextromethadone, as well as pharmaceutically acceptable salts thereof, are particularly preferred.

In a further preferred embodiment of the multilayer tablet according to the invention, at least the second active-substance layer is formed by direct compression, since this is particularly inexpensive.

In a further embodiment, the multilayer tablet additionally comprises at least one stabilizer, which protects the naloxone. In a preferred embodiment, the at least one stabiliser is selected from the list comprising sulphur dioxide, sodium sulphite, sodium bisulphite, ascorbic acid and its derivatives and tocopherol, as well as its water- and fat-soluble derivatives, such as, for example, tocopherol acetate, sulphites, bisulphites and hydrogen sulphites of alkali, alkaline earth metals or other metals, paraben, BHA, BHT, gallates, as well as lower fatty acids, fruit acids, phosphoric acids, sorbic and benzoic acids as well as their salts, esters, derivatives and isomeric compounds, ascorbyl palmitate, lecithins, mono- and polyhydroxylated benzene derivatives, ethylenediaminetetraacetic acid and salts thereof, citraconic acid, cysteine, L-cysteine, conidendrin, diethyl carbonate, methylenedloxyphenols, cephalin, β,β-dithiopropionic acid, biphenyl and other phenyl derivatives.

In a further embodiment, the multilayer tablet additionally comprises at least one stabiliser, which protects the matrix. In a preferred embodiment, the at least one stabilizer is selected from the list comprising butylated hydroxytuluol, sulphur dioxide, sodium sulphite, sodium bisulphite, ascorbic acid and its derivatives and tocopherol, as well as its water- and fat-soluble derivatives, such as, for example, tocopherol acetate, sulphites, bisulphites and hydrogen sulphites of alkali, alkaline earth metals and other metals, paraben, BHA, BHT, gallates as well as lower fatty acids, fruit acids, phosphoric acids, sorbic and benzoic acids and their salts, esters, derivatives and isomeric compounds, ascorbyl palmitate, lecithins, mono- and polyhydroxylated benzene derivatives, ethylenediaminetetraacetic acid and their salts, citraconic acid, cysteine, L-cysteine, conidendrin, diethyl carbonate, methylenedioxyphenole, cephalin, β,β-dithiopropionic acid, biphenyl and other phenyl derivatives.

In a further embodiment, the multilayer tablet comprises at least one additive, wherein the additive is an emetic or a pungent agent drug, in a preferred embodiment, the composition comprises an additive, wherein this additive is a pungent agent, selected from the group comprising Allii sativi bulb, Asari rhizome cum herba, Calami rhizoma, capsici fructus (capsicum) capsici fructus acer (cayenne pepper), Rhizome Curcumae Longae, Curcumae xanthorrhizae rhizoma, Galangae rhizoma. Semen Myristicae, Piperis nigri fructus (pepper), Sinapis albae (Erucae) Semen, Sinapis nigrae semen, Zedoariae rhizoma and Zingibers rhizoma, preferably from the group consisting of capsici fructus (capsicum), capsici fructus acer (cayenne pepper) and Piperis nigri fructus (pepper).

In a preferred embodiment, the multilayer tablet comprises at least one additive, wherein this additive is an emetic. In a preferred embodiment, the emetic is based on one or several substances from radix ipecacuanha (ipecac). In a preferred embodiment, the emetic is based on the substance emetine, in an alternative embodiment, the emetic is apomorphine.

In a further embodiment, the multilayer tablet comprises a dye. In a preferred embodiment, the dye is selected from a group comprising red iron oxide, black iron oxide and indigo carmine.

In a further embodiment, the multilayer tablet additionally comprises at least one non-steroid antirheumatic or an antihistamine.

In an alternative embodiment, the multilayer tablet additionally comprises at least one water-soluble lubricant. In a preferred embodiment, the multilayer tablet comprises at least one water-soluble lubricant selected from the group comprising adipic acid, fumaric acid, sodium benzoate and macrogols.

In a further preferred embodiment of the invention, the multilayer tablet is designed as a once-a-day formulation.

In a further preferred embodiment of the invention, the multilayer tablet is designed as a twice-a-day formulation.

In a further preferred embodiment, the multilayer tablet is contains from 0.1 to 500 mg of opioid agonist, or of a pharmaceutically acceptable salt thereof, and from 0.1 to 500 mg of opioid antagonist, or of a pharmaceutically acceptable salt thereof, particularly preferred is a ratio (agonist:antagonist) of 1:10 to 10:1.

The present invention further relates to a method for producing the multilayer tablet of the invention, comprising at least the steps of providing a first tablet mass that comprises an opioid agonist, or a pharmaceutically acceptable salt thereof, as an active substance, as well as a release retardant;

providing a second tablet mass that comprises an opioid antagonist, or a pharmaceutically acceptable salt thereof, as an active substance, as well as a release retardant;

filling a first filling shoe of s tablet pressing tool with the first tablet mass and a second filling shoe of the tablet pressing tool with the second tablet mass:

pressing of the first and second table mass to obtain a multilayer tablet.

The present invention further relates to a method for producing the multilayer tablet of the invention, comprising at least the steps of providing a first tablet mass that comprises an opioid agonist, or a pharmaceutical acceptable salt thereof, as an active substance, wherein the opioid agonist, or the pharmaceutically acceptable salt thereof, in the first tablet mass is present in the form of pellets which contain the opioid agonist and onto which a release retardant layer is applied;

providing a second tablet mass that comprises an opioid antagonist, or a pharmaceutically acceptable salt thereof, as an active substance, as well as a release retardant;

filling a first filling shoe of a tablet pressing tool with the first tablet mass and a second filling shoe of the tablet pressing tool with the second tablet mass;

pressing of the first and second table mass to obtain a multilayer tablet.

The present invention further relates to the use of the multilayer tablet of the invention for the treatment of pain and for the simultaneous treatment of opioid-induced constipation.

In a preferred embodiment, the second tablet mass has a $IC_{50}/C_{max}$ value of at least 30. In a more preferred embodiment, the second tablet mass has an $IC_{50}/C_{max}$ value of at least 35. In an even more preferred embodiment, the second tablet mass has an $IC_{50}/C_{max}$ value of at least 40. In the most preferred embodiment, the second tablet mass has an $IC_{50}/C_{max}$ value of at least 50.

The following examples serve to illustrate the invention.

EXAMPLES

Oral Composition

The following examples are used in conjunction with the drawing to illustrate the invention. It shows:

FIG. 1: Release profiles of the tablets according to examples 1 and 2.

EXAMPLE 1

Tablets with the following composition were produced:

| Substance | Function | Weight [mg] |
|---|---|---|
| Naloxone hydrochloride | Active substance | 48.00 |
| Glycerol dibehenic acid ester | Release retardant | 204.64 |
| Colloidal silicon dioxide | Flow regulator | 19.00 |
| Magnesium stearate | Lubricant | 2.36 |
| | Total weight of the tablet | 274.00 |

The components naloxone hydrochloride and glycerol dibehenic acid ester were sieved and mixed together. First the sieved Colloidal silicon dioxide and then the magnesium stearate were mixed into the resulting mixture. The thus obtained mixture was pressed into a tablet using a conventional tablet pressing tool.

EXAMPLE 2

Tablets with the following composition were produced with the same method as in example 1:

| Substance | Function | Weight [mg] |
|---|---|---|
| Naloxone hydrochloride | Active substance | 12.00 |
| Kollidon ® SR | Release retardant | 63.16 |
| Vivapur 200 | Filler | 7.00 |

-continued

| Substance | Function | Weight [mg] |
|---|---|---|
| Colloidal silicon dioxide | Flow regulator | 1.24 |
| Magnesium stearate | Lubricant | 0.60 |
| | Gesamtgewicht der Tablette | 84.00 |

Kollidon ® SR consisting of 80 wt.-% polyvinyl acetate, 19 wt.-% povidone, 0.8 wt.-% sodium lauryl sulfate and 0.2 wt.-% Colloidal silicon dioxide.

EXAMPLE 3

Coated two-layer tablets with the following composition were produced;

| Substance | Function | Weight [mg] |
|---|---|---|
| Naloxone layer | | |
| Naloxone Hydrochloride | Active substance | 3.00 |
| Kollidon ® SR | Release retardant | 17.00 |
| Glycerol dibehenic acid ester | Release retardant | 4.75 |
| Colloidal silicon dioxide | Flow regulator | 0.60 |
| Magnesium stearate | Lubricant | 0.15 |
| | Total weight of the naloxone layer | 25.5 |
| Placebo layer | | |
| Sugar pellets (diameter: 500-600 μm) | Carrier | 10.00 |
| Hypromellose | Filler | 10.00 |
| microcrystalline cellulose | Filler | 10.00 |
| Colloidal silicon dioxide | Flow regulator | 0.25 |
| Magnesium stearate | Lubricant | 0.25 |
| | Total weight of the placebo layer | 30.50 |
| | Total weight of the two-layer tablet core | 56.00 |
| Opadry ® | Tablet coating | 3.00 |
| | Total weight of the two-layer tablet | 59.00 |

The components of the naloxone layer, that is, naloxone hydrochloride, Kollidon ® SR, glycerol dibehenic acid ester, colloidal silicon dioxide and magnesium stearate were sieved and blended together to form a first powdery mixture. Further, the components of the placebo layer: sugar pellets, hypromellose, microcrystalline cellulose, colloidal silicon dioxide and magnesium stearate were sieved and mixed together to form a second powdery mixture.
The first and the second mixture were pressed with a conventional two-layer tablet press to obtain the two-layer tablet core. The thus obtained two-layer tablet core was coated to obtain the two-layer tablet.

Release Profile

The in vitro release profiles of the tablets according to examples 1 and 2 were determined using a the paddle stirrer apparatus (apparatus 2) with the paddle stirrer method according to Ph. Eur. (Europäsches Arzneibuch, 7th edition, 3rd supplement, 2.9.3 "Wirkstofffreisetzung aus festen Arzneiformen", pages 5519-5526) at 75 rpm in 500 ml 0.1 N hydrochloric acid at 37° C. The amount of released naloxone was determined by UV-detectlon at 220 nm.

The in vitro release profiles of the tablets according to examples 1 (♦) and 2 (×) are shown in FIG. 1.

Multilayer Tablets

EXAMPLE 1

Coated two-layer tablets of the following composition were produced:

| Substance | Function | Weight [mg] |
|---|---|---|
| Oxycodone layer | | |
| Sustained-release oxycodone pellets (containing 3 mg oxycodone HCl) | Active substance | 10.00 |
| microcrystalline cellulose | Filler | 24.50 |
| Colloidal silicon dioxide | Flow regulator | 0.25 |
| Magnesium stearate | Lubricant | 0.25 |
| | Total weight of the oxycodone layer | 35.00 |
| Naloxone layer | | |
| Naloxone hydrochloride | Active substance | 3.00 |
| Kollidon ® SR | Release retardant | 21.75 |
| Colloidal silicon dioxide | Flow regulator | 0.50 |
| Magnesium stearate | Lubricant | 0.25 |
| | Total weight of the naloxone layer | 25.50 |
| | Total weight of the two-layer tablet core | 60.50 |
| Opadry II ® | Tablet coating | 2.50 |
| | Total weight of the two-layer tablet | 63.00 |

The components of the oxycodone layer, that is, sustained release oxycodone pellets, microcrystalline cellulose, colloidal silicon dioxide and magnesium stearate were sieved and blended together to form a first powdery mixture.
Further, the components of the naloxone layer: naloxone hydrochloride, Kollidon ® SR, colloidal silicon dioxide and magnesium stearate were sieved and mixed together to form a second powdery mixture.
The first and the second mixture were pressed with a conventional two-layer tablet press to obtain the two-layer tablet core. The thus obtained two-layer tablet core was coated with the coating material Opadry II ® that had been dissolved in water at a temperature of 30° C. to 50° C. to obtain the two-layer tablet.

The sustained-release oxycodone pellets had the following composition and were prepared as known in the art:

| Substance | Function | Weight [mg] |
|---|---|---|
| Oxycodone pellets | | |
| Oxycodone hydrochloride | Active substance | 3.00 |
| Pellets neutral | Carrier | 2.50 |
| Povidone | Binder | 0.50 |
| Retardant layer | | |
| Ethylcellulose | Retarding agent | 3.00 |
| Hydroxypropylcellulose | | 0.50 |
| Triethyl citrates | | 0.50 |
| | Total weight of the sustained release oxycodone pellets | 10.00 |

Koilidon® SR consists of 80 wt.-% polyvinyl acetate, 19 wt.-% povidone, 0.8 wt.-% sodium lauryl sulfate and 0.2 wt-% Colloidal silicon dioxide.

Opadry II® consists of polyvinyl alcohol, Iron oxide or titanium dioxide, Macrogol and talc.

EXAMPLE 2

Coated two layer tables of the following composition were produced as in example 1:

| Substance | Function | Weight [mg] |
|---|---|---|
| Oxycodone layer | | |
| Sustained-release oxycodone pellets (containing 9 mg oxycodone HCl) | Active substance | 30.00 |
| microcrystalline cellulose | Filler | 30.00 |
| Colloidal silicon dioxide | Flow regulator | 1.00 |
| Magnesium stearate | Lubricant | 1.00 |
| | Total weight of the oxycodone layer | 62.00 |
| Naloxone layer | | |
| Naloxone hydrochloride | Active substance | 6.00 |
| Glycerol dibehenic acid ester | Release retardant | 23.00 |
| microcrystalline cellulose | Filler | 20.00 |
| Colloidal silicon dioxide | Flow regulator | 1.50 |
| Magnesium stearate | Lubricant | 0.50 |
| | Total weight of the naloxone layer | 51.00 |
| | Total weight of the two-layer tablet core | 113.00 |
| Opadry II ® | Tablet coating | 8.00 |
| | Total weight of the two-layer tablet | 121.00 |

EXAMPLE 3

Coated two layer tables of the following composition were produced as in example 1:

| Substance | Function | Weight [mg] |
|---|---|---|
| Oxycodone layer | | |
| Sustained-release oxycodone pellets (containing 24 mg oxycodone HCl) | Active substance | 80.00 |
| microcrystalline cellulose | Filler | 242.00 |
| Colloidal silicon dioxide | Flow regulator | 4.00 |
| Magnesium stearate | Lubricant | 4.00 |
| | Total weight of the oxycodone layer | 330.00 |
| Naloxone layer | | |
| Naloxone hydrochloride | Active substance | 48.00 |
| microcrystalline cellulose | Filler | 84.00 |
| Kollidon ® SR | Release retardant | 204.00 |
| Colloidal silicon dioxide | Flow regulator | 10.00 |
| Magnesium stearate | Lubricant | 2.00 |
| | Total weight of the naloxone layer | 348.00 |
| | Gesamtgewicht des Zweischichttablettenkerns | 678.00 |
| Opadry ® | Tablet coating | 22.00 |
| | Total weight of the two-layer tablet | 700.00 |

FIGURE LEGEND

FIG. 1: Release profile of naloxone from the composition according to the invention; (x) example 1, (♦) example 2.

The invention claimed is:

1. A solid oral pharmaceutical composition comprising naloxone, or a pharmaceutically acceptable salt thereof, as an active substance, wherein the composition releases the active substance in a prolonged manner, and the in vitro release rate of the active substance naloxone, measured using the paddle stirrer method according to Ph. Eur, at 75 rpm in 500 ml 0.1 N hydrochloric acid at 37° C., of 0% to 75% in 2 h, of 3% to 95% in 4 h, of 20% to 100% in 10 h, of 30% to 100% in 16 h, of 50% to 100% in 24 h, and of more than 80% in 36 h, wherein the composition has a $IC_{50}/C_{max}$ value of at least 40, wherein the composition comprises a matrix, wherein the matrix comprises glycerol dibehenic acid ester as matrix-forming agent, and wherein the mass ratio of naloxone to glycerol dibehenic acid ester is 1:2.5.

2. A composition according to claim 1, wherein the composition releases the active substance naloxone independently of the ambient pH of the gastrointestinal tract.

3. A composition according to claim 1, wherein the composition has an in vitro release rate of the active substance naloxone of 0% to 50% in 2 h, of 5% to 95% in 4 h, of 20% to 90% in 10 h, of more than 70% in 18 h, and of more than 80% in 24 h.

4. A composition according to claim 1, wherein the composition has an in vitro release rate of the active substance naloxone of 0% to 38% in 2 h, of 5% to 55% in 4 h, and of 20% to 75% in 10 h.

5. A composition according to claim 1, wherein the composition has an in vitro release rate of the active substance of 0% to 50% in 1 h, of 10% to 95% in 4 h, of 35% to 100% in 8 h, of 55% to 100% in 12 h, of 70% to 100% in 16 h, and of more than 90% in 24 h.

6. A composition according to claim 1, wherein the composition has an in vitro release rate of the active substance of 0% to 30% in 1 h, of 0% to 40% in 2 h, of 3% to 55% in 4 h, of 10% to 65% in 8 h, of 20% to 75% in 12 h, of 30% to 88% in 18 h, of 50% to 100% in 24 h, and of more than 80% in 36 h.

7. A composition according to claim 1, wherein a matrix releases the active ingredient in a prolonged manner.

8. A composition according to claim 7, wherein the matrix comprises one or several matrix-forming agents selected from the group consisting of cellulose esters, polyvinylpyrrolidone/polyvinyl acetate mixtures, methacrylate-acrylate copolymers, waxes, fats such as glycerol esters, and fatty alcohols.

9. A composition according to claim 8, wherein the matrix comprises polyvinylpyrrolidone/polyvinyl acetate mixtures as matrix-forming agent.

10. A composition according to claim 8, wherein the matrix comprises glycerol dibehenic acid ester as matrix-forming agent.

11. A composition according to claim 1, wherein the composition is formed by direct compression.

12. A composition according to claim 1, wherein the composition is designed as a once-a-day formulation.

13. A composition according to claim 1, wherein the composition is designed as a twice-a-day formulation.

14. A multilayer tablet comprising at least
   a first active substance-containing layer, which contains as an active substance an opioid agonist, or a pharmaceutical acceptable salt thereof; and a second active substance-containing layer, which contains as an active substance an opioid antagonist, or a pharmaceutically acceptable salt thereof, wherein the first and the second active substance-containing layers release the active substance in a prolonged manner, and the second active substance-containing layer has a $IC_{50}/C_{max}$ value of at least 40, wherein the composition comprises a matrix, wherein the matrix comprises glycerol dibehenic acid ester as matrix-forming agent, and wherein the mass ratio of naloxone to glycerol dibehenic acid ester is 1:2.5.

15. A multilayer tablet, wherein the second active substance-containing layer comprises a composition according to claim 1.

16. A multilayer tablet according to claim 14, wherein the opioid agonist is selected from the group consisting of hydrocodone, morphine, hydromorphone, oxycodone, buprenorphine, codeine, fentanyl, levorphanol, meperidine, methadone, levomethadone and dextromethadone as well as their pharmaceutically acceptable salts.

17. A method for the production of a multilayer tablet according to claim 14, comprising the steps of
providing a first tablet mass that comprises an opioid agonist, or a pharmaceutically acceptable salt thereof, as an active substance, as well as a release retardant;
providing a second tablet mass that comprises an opioid antagonist, or a pharmaceutically acceptable salt thereof, as an active substance, as well as a release retardant, characterised in that the second table mass has a $IC_{50}/C_{max}$ of at least 40;
filling a first filling shoe of a tablet pressing tool with the first tablet mass and a second filling shoe of the tablet pressing tool with the second tablet mass;
pressing of the first and second table mass to obtain a multilayer tablet.

18. A method for the production of a multilayer tablet according to claim 14, comprising the steps of
providing a first tablet mass that comprises an opioid agonist, or a pharmaceutically acceptable salt thereof, as an active substance, wherein the opioid agonist, or the pharmaceutically acceptable salt thereof, in the first tablet mass is present in the form of pellets which contain the opioid agonist and onto which a release retardant layer is applied;
providing a second tablet mass that comprises an opioid antagonist, or a pharmaceutically acceptable salt thereof, as an active substance, as well as a release retardant, characterised in that the second table mass has a $IC_{50}/C_{max}$ of at least 40;
filling a first filling shoe of a tablet pressing tool with the first tablet mass and a second filling shoe of the tablet pressing tool with the second tablet mass;
pressing of the first and second table mass to obtain a multilayer tablet.

19. A method of treating opioid-induced constipation comprising administering the solid oral pharmaceutical composition of claim 1.

20. A method of treating opioid-induced constipation comprising administering the multilayer tablet of claim 14.

* * * * *